United States Patent [19]
Wetegrove et al.

[11] Patent Number: 5,264,917
[45] Date of Patent: Nov. 23, 1993

[54] MONITORING OF FILM FORMERS

[75] Inventors: Robert L. Wetegrove, Winfield; Rodney H. Banks, Naperville, both of Ill.

[73] Assignee: Nalco Chemical Company, Naperville, Ill.

[21] Appl. No.: 842,655

[22] Filed: Feb. 27, 1992

[51] Int. Cl.$^5$ .............................................. G01B 11/06
[52] U.S. Cl. .................................. 356/382; 356/244; 356/434; 356/440; 250/341; 250/576
[58] Field of Search ...................... 356/36, 38, 70, 244, 356/381, 382, 432, 434, 440; 250/340, 341, 573, 576

[56] References Cited

U.S. PATENT DOCUMENTS

| | | | |
|---|---|---|---|
| 2,489,286 | 11/1949 | Grant, Jr. ............................... | 356/38 |
| 2,562,901 | 8/1951 | Fischer .................................. | 356/38 |
| 2,898,803 | 8/1959 | Morrison ............................... | 356/38 |
| 4,135,100 | 1/1979 | Harada et al. ......................... | 356/440 |
| 4,916,317 | 4/1990 | Gabriel et al. ......................... | 356/445 |
| 4,941,742 | 7/1990 | Schrader et al. ...................... | 356/38 |
| 4,998,141 | 3/1991 | Altmann ................................ | 356/440 |

FOREIGN PATENT DOCUMENTS 0029192  3/1978  Japan ...................................... 356/440

*Primary Examiner*—F. L. Evans
*Attorney, Agent, or Firm*—Kinzer, Plyer, Dorn, McEachran & Jambor

[57] ABSTRACT

Method and apparatus for monitoring film formers in an opaque process stream by immersing a segment of a transparent eccentrically mounted rotatable disc in the fluid stream, allowing time to accumulate film formers, then rotating the disc to expose the previously immersed section to optical monitoring by which a sample transmittance may be compared to a reference transmittance; the disc may have a segment presenting a hydrophilic surface and another segment presenting a hydrophobic surface so that different kinds of film formers may be monitored.

7 Claims, 2 Drawing Sheets

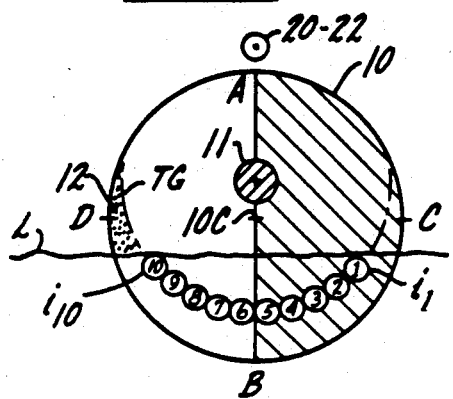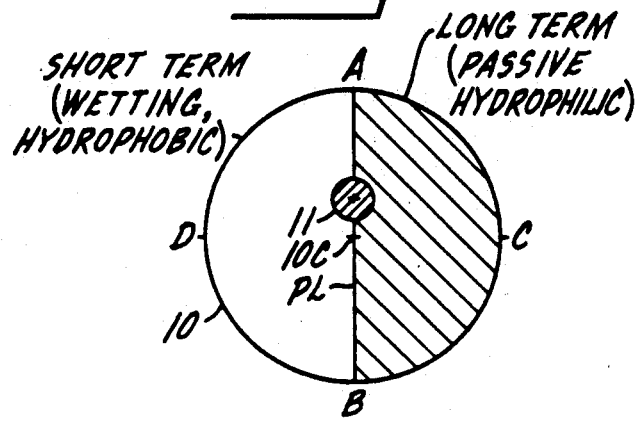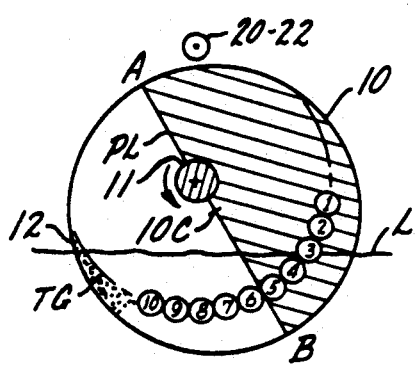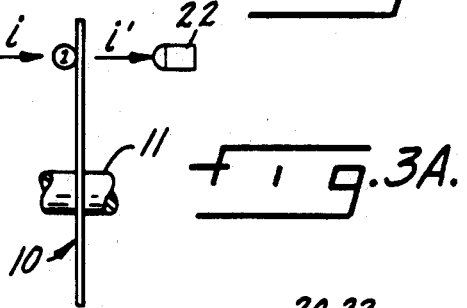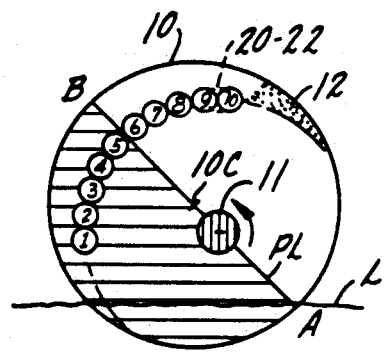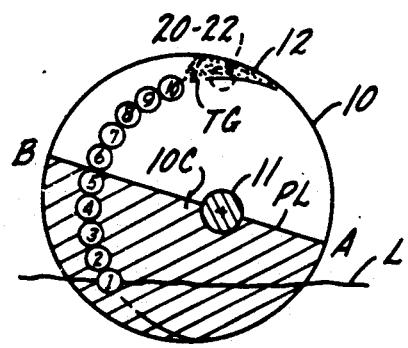

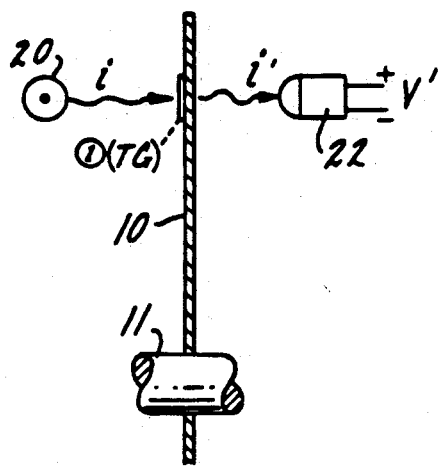
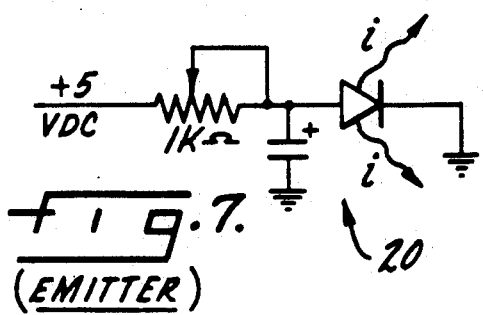
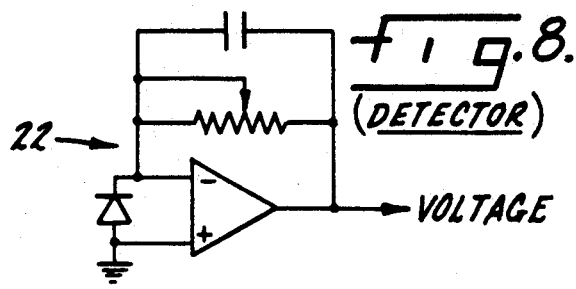
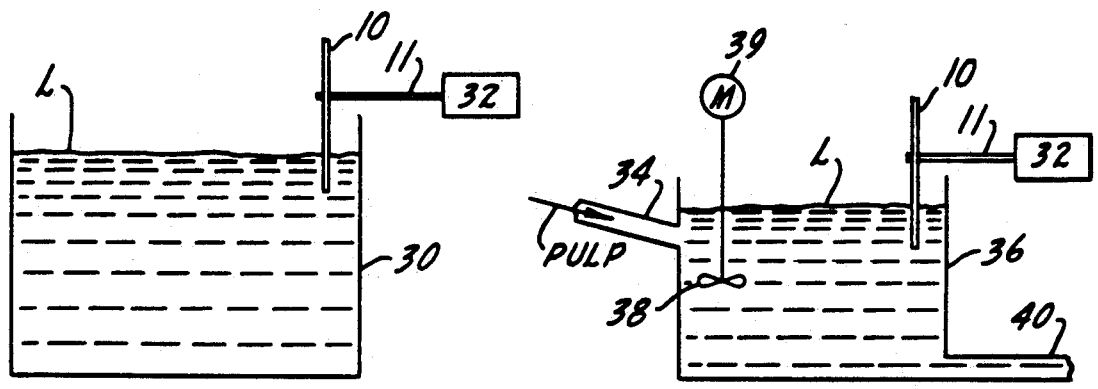
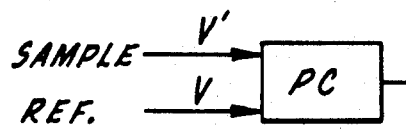
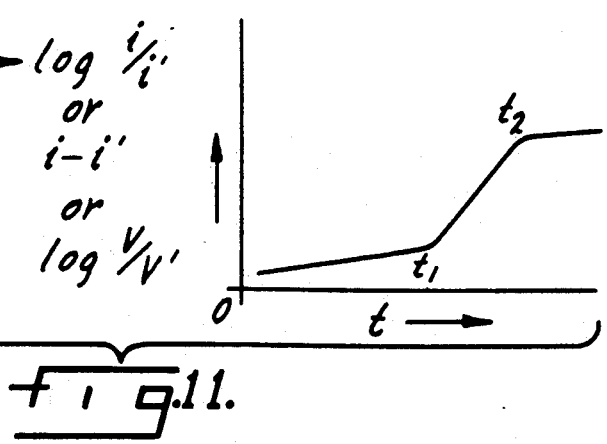

MONITORING OF FILM FORMERS

BACKGROUND OF THE INVENTION

This invention relates to the determination of unwanted deposit formations in an opaque fluid stream employed for industrial or manufacturing processes. Determination is made in situ or by real time analysis, or near to it, rather than by extracting a sample of the fluid for external laboratory analysis elsewhere.

There are numerous examples of industrial fluid streams confined by a conduit for manufacturing purposes where entrained biological growths or organic impurities deposit on and reduce the efficiency of equipment employed in processing the fluid. Not only that, the finished product may be contaminated by the film.

A good example is paper making machinery when the confining conduit is the paper machine itself. Bacteria colonies, protozoa and other simple life forms become entrained in the pulp. These feed and thrive on indigenous substances such as proteins, oils, carbohydrates and polysaccharides. The colony expands and becomes a gummy, sticky biofilm which can trap other particles and deposit on the walls of the chest and other equipment in the pulp confining conduit downstream of the chest. The equipment becomes fouled. The unwanted films are loosened due to turbulence and become part of the paper, resulting in grade degradation. Pitch (hydrophobic contaminants) present as part of the wood fibers is another source of an unwanted organic deposits.

The same phenomena are involved in cutting oils as another example. The purity and efficiency of the oil are degraded, the surfactant which maintains the cutting oil as an emulsion is adversely affected, and film deposits on the workpiece being machined.

REFERENCE TO RELATED APPLICATION

In our co-pending application Ser. No. 07/754,016, filed Sep. 3, 1991, now U.S. Pat. No. 5,185,533, we address the problem of film formers in a transparent process stream such as cooling tower water, undertaking a double beam transmittance comparison (reference and sample) to determine film build-up. In our co-pending application Ser. No. 07/726,592, filed Jul. 8, 1991 now issued as U.S. Pat. No. 5,155,555, we address the same problem (film growth or build-up) in an opaque stream where we measure light reflectance to determine film build-up.

We have now succeeded in deriving a procedure by which an opaque stream can be monitored for film prevalence by light transmittance rather than reflectance, constituting the subject matter of the present invention.

SUMMARY OF THE INVENTION

The film formers may be of slow growth (long term) such as bacteria colonies which slowly accumulate on the process equipment. They may be of short term, such as pitch, which quickly adheres. Under and in accordance with the present invention, the prevalence of opaque film formers in a process stream is monitored by immersing in the stream a segment of a transparent (or translucent) disc for a predetermined time. The selected time for immersion is sufficient to allow the slow-growth film formers to collect on the process equipment. Then, by rotating the disc, the segment bearing the film can be targeted by a light beam. Since the disc is transparent (or of equivalent translucence) the beam will pass (transmit) light of an intensity inversely proportional to the thickness of the film. The transmitted light can be sensed for intensity, producing a voltage analog of film thickness as will be explained. Also, as will be explained, the configuration is such that short term occlusions can also be measured. If the thicknesses exceed a predetermined allowance, a microprocessor will activate a pump which feeds to the stream a treating agent which combats, disperses or otherwise controls the film former(s) to an acceptable standard or tolerance level.

In more specific terms, the invention is characterized by a disc (or coupon of equivalent configuration) which will transmit light in spite of an occluding film. The disc is partly submerged in the opaque process stream and is preferably supported for rotation about an eccentric axis. If rotated by a stepping motor, the disc may be turned at selected intervals so that the segment previously immersed is exposed for monitoring by an optical sensor which measures the intensity of light (originated from a source) transmitted through one or more targeted areas containing the film sample. Less light is transmitted through a spot or target having greater film thickness. The exposed surface may be indexed by the stepping motor so that multiple spots on the disc may be targeted, obtaining an average of transmittance readings of accumulated fouling.

By maintaining immersion for a relatively long term period, the immersed segments simulate exposure of the equipment (process conduit and attendant parts) to long term or passive accumulations of fouling. Then, by rotating the disc, after taking a long-term average of transmittance, or even a single transmittance reading corresponding to long term (passive) immersion, the normally non-immersed segment on the disc may be monitored as a short-term (wetting) surface simulating turbulent or mere wetting film conditions. This difference between long term and short term film conditions can be of significance. The long term film may be taken as one in which the bacterial identity or growth is not severe and film build-up is slow. In comparison, the normally dry segment will quickly and easily capture the most tenacious or pernicious film formers such as organic pitch, one of the more inimical deposit formers.

PRIOR ART

To the best of our knowledge there is no art pertinent to the present invention characterized by determining transmittances through a transparent disc having successive long and short term immersions in an opaque fluid containing film formers; one portion of the disc is employed to occlude the less innocuous or passive film formers, and another portion of the disc is employed to occlude strong or pernicious film formers.

There are systems for detecting internal film formation, namely, U.S. Pat. Nos. 4,912,332 and 3,757,210 but these disclosures do not comply with the characterizing features of the present invention.

BRIEF DESCRIPTION OF THE DRAWING

FIG. 1 is a diagram of the immersed disc in its normal (start) position, partly submerged in an opaque fluid to be sampled;

FIG. 1A is a diagram of the disc illustrating its division into hydrophilic and hydrophobic segments;

FIGS. 2 through 6 are diagrams of successive, different positions assumed by the disc as it is being monitored;

FIGS. 7 and 8 are schematic views of the optic transmittance principles which feature in the present invention;

FIGS. 9 and 10 are schematic views of the invention in practice; and

FIG. 11 is a diagram showing measurement of film thickness, an analog of film thickness vs. time.

BEST MODE: INSTRUMENTATION

Characterization of the present invention is best explained in terms of the schematics shown in the various figures.

A rotatable, transparent disc 10, FIG. 1, having a center 10C, is secured eccentrically to a shaft 11. The disc is to be partly immersed in a process stream having a surface level L. The disc, FIG. 1A, is divided into two segments. As will be described in more detail, one segment of the disc is hydrophilic in character, the other of hydrophobic character. The segments are to be monitored by a light emitter-detector couple (20-22, FIGS. 3A and 6) described below.

Segment ACB of the disc 10 (shaded) is an acrylic, presenting a surface (deemed hydrophilic) to simulate typical process equipment such as employed in a paper mill for the so-called machine chest (chest) and other equipment which tends to be fouled by organic film formers. Segment ACB could also be glass or polycarbonate. It is sufficient that segment ACB will indeed tend to accumulate the long term, passive film formers substantially proportional to the equipment exposed to the process fluid which is deemed opaque in terms of light transmittance.

The other segment ADB (unshaded) presents a hydrophobic surface, such as polyethylene, polytetrafluorethylene or polypropylene. This segment will tend to accept the wetting or short term species such as pitches. The two segments are easily bonded along a parting line PL, FIG. 1A, which may be taken as the diameter AB of the disc. The exact position of the parting line and precise depth of immersion are not critical. However, for the configuration and depth of immersion shown in FIG. 1, there is an immersed hydrophilic portion BC below level L and an immersed hydrophobic segment DB below level L, of equal area. Also, there is a cusp area 12 in the hydrophobic segment of the disc which has a role to be described.

With the disc immersed in an opaque fluid having surface level L (e.g. the paper pulp in the chest of a paper making machine), the immersed (hydrophilic) portion (CB) will tend to be contaminated by hydrophilic deposit formers which are present. The immersed hydrophobic portion (DB) will tend to accumulate the hydrophobic film formers.

Referring again to FIG. 1, an arbitrary arc shown by dashed line represents a targeting arc. Arbitrarily there are ten targets, circle 1 through circle 10 also denoted i, ... i₁₀; circle 5 (hydrophilic) is just short of midway and circle 6 is on the immediate other side, the hydrophobic side. The targets lie on the same radius from the eccentric rotation center 11, all on the targeting arc TG. If the disc is rotated about the eccentric axis 11, following a long term immersion, the arc to be targeted emerges, FIGS. 2, 3 and 4, and target spots fouled by the long term occluded film are to be intercepted one after another by a light beam of intensity i, FIG. 3A, to take an average of the intensity i' of the emergent beam, the intensity of which is reduced by the thickness of the targeted film. There are circumstances of course where only one reading may be enough.

In FIG. 2, target circle 1 has not yet attained a position where it can be spotted (illuminated or intercepted) by the beam of light. In comparison, it can be assumed that the center of target circle 1, FIGS. 3 and 3A, has attained the position where it can be spotted by the monitoring beam.

In FIG. 4, target circle 9 (hydrophobic) has been monitored and target circle 10 is moving to a position where it will be intercepted by the spotting beam. Thus, in summary at this point, targets 1 through 5 present the hydrophilic occlusions to be monitored and averaged, whereas targets 6 through 10 represent the hydrophobic targets to be monitored and averaged.

It will be realized of course that there are an infinite number of arcs and targets that can be monitored within the hydrophilic segment (CB) to determine the long term (passive, hydrophilic) film thicknesses. Likewise as to the hydrophobic segment BD.

The disc, after immersion, can be stepped (rotation-wise) quickly during monitoring, a matter of a few minutes more or less. Consequently, the left-hand cusp 12, which is of hydrophobic material, FIG. 1, will have a short term exposure to the process stream, capturing those tenacious hydrophobic species which tend quickly to adhere. Cusp 12 eventually starts to emerge, FIG. 3, is approaching the spotting beam, FIG. 4, and has attained the spotting beam position, FIG. 5. Cusp area 12 is now positioned for monitoring (alternatively or successively) the thicknesses of selected targets which underwent short term wetting in the course of movement through the process water. These targets carry tenacious or pernicious film formers such as organic pitches.

The reason for the eccentric axis concerns the need to so position the light probe or sensing couple 20-22, FIG. 1, free of the edge of the disc when at home position, FIG. 1. This enables the intensity of the light beam hereinafter described, to be measured in air as a base line prior to each cycle for measuring the thickness of the occluded film on the disc 10. There may be interference particles in the air, optical surfaces may be contaminated, or the source intensity may have changed from the previous cycle.

BEST MODE: DETAILS

According to Beer's Law, the light absorbed by an absorbing material is proportional to its thickness. This law allows the thickness of the film on the disc 10 to be measured quantitatively by casting a light beam of known intensity i on to of less intensity, i'. The value log (i/i') is a measure of the film thickness. These intensity values will have corresponding voltage analogs V and V', as to which there is further comment below.

Referring to FIG. 6, the disc 10, after long term immersion, has been rotated to a position corresponding to FIG. 3, and at this position target circle 1 is presented to a light source (IR, VU or visible) 20 which casts or directs a reference beam of intensity i on target circle 1. A sensor 22 responds to the transmitted light, of weakened intensity i', which can be converted by the sensor to a voltage analog V'.

A programmer, now shown, then activates the stepping motor (not shown) to index the disc counterclockwise so that another successive hydrophilic target is presented to the light source 20. The same beam (intensity i) is cast or directed onto the new target and through disc 10. Transmittance intensity i' is again sensed.

The circuitry for monitoring is disclosed in our application Ser. No. 07/754,016 filed Sep. 3, 1991 which is incorporated by reference herein. Briefly, the light source 20 may be an infrared (890 nm) light emitting diode (LED), No. L2690 supplied by Hamamatsu. The wavelength (890 nm) is chosen so that the water absorption band (960 nm) will not interfere. The circuit is shown in FIG. 7. The current can be adjusted by the trim potentiometer between 100 ma and 3.6 ma, so the detector voltage will be scaled to 0-10 volts. The detector 22 is a photodiode, preferably with a large light sensitive area. Preferred is S2281 series of Hamamatsu, having a sensitive area of about 100 mm$^2$. The circuitry is shown in FIG. 8 and it may be mentioned that a long wave filter (850 nm cut-off, not shown) is preferably placed in front of the photodiode to eliminate ambient light interference.

Prior to any monitoring sequence, the beam i will be directed through a clean untarnished disc 10 at each target spot. By doing this any imperfections at each target area will be accounted for, especially as the disc will be used over and over again. Also, the intensity of the beam in air will first be measured, FIG. 1, to determine the base line intensity i.

The two voltage analogs corresponding to i (calibrated) and i' can be used by a computer to calculate log (i/i') representing the thickness of the film at any target spot.

The measurements can be repeated sequentially for the targets within the two segments, likewise for a cusp section such as 12. By so doing, an average of film thicknesses can be taken for the hydrophilic section which simulates slow biofouling build-up on the equipment, and likewise an average film thickness within the hydrophobic section which simulates quick capture of organics such as pitches and oils entrained in the process stream.

In the instance of monitoring a paper pulp stream, the disc 10 could be immersed in the so-called water or machine chest 30, FIG. 9, shaft 11 being indexed by a stepping motor 32. However, the paper pulp stream to be monitored could be drained by a pipe 34, FIG. 10, to a separate test or sampling tank 36 where turbulence is simulated by an impeller 38 driven by a motor 39. The return line is indicated by reference character 40 assuring true flow and process conditions.

DATA PROCESSING AND PROGRAMMING

It is appropriate to elaborate on the relationship of transmittance and absorbance. Absorbance is the ability of a surface to absorb light (or radiation), and in this instance the surface is the film on the disc. Transmittance is the fraction of light that having entered the film (herein i) emerges from the far side of the disc (i') where the detector is located.

Expressed mathematically, absorbance is the negative logarithm (common log) of transmittance. Thus, $$\frac{\text{Sample voltage}}{\text{Reference voltage}} \times 100\% = \frac{V'}{V} \times 100\% = \quad \text{(Eq. 1)}$$

% transmittance and

-continued $$\log \frac{V}{V'} = \text{absorbance} \quad \text{(Eq. 2)}$$

so that $$\log V - \log V' = \text{biofilm absorbance} \quad \text{(Eq. 3)}$$

In other words, biofilm thickness is proportional to its absorbance. Since log V/V' (absorbance) is measured under and in accordance with the present invention (see FIG. 11) the rate of film build-up can be monitored.

There may be circumstances where only one reading, whether hydrophilic or hydrophobic, will be sufficient. However, an average is better and consequently multiple readings should be taken to obtain an average i'.

In any event, the significant datum, each time, is the difference or ratio of i (calibrated) and i' which can be a voltage analog (millivolts, mv) representing film thickness. Thus, as shown in FIG. 11, the voltages V' (target sample) and V (reference or base line) emitted by the detector 22, FIGS. 7 and 8, can be microprocessed at PC to determine the value for each reading, namely, $$\text{Absorbance (Abs)} = \log i/i' = \log V/V'$$

Since absorbance is proportional to film thickness (Eq. 4), the microprocessor can be programmed to resolve any of the analogs by which the intensity of the light transmitted through the sample or target film, and through the disc, is compared to the reference intensity i transmitted through the clean or clear disc. This equivalency of values is shown by the computer printout or display in FIG. 11 where the equivalents of film thickness are represented by the vertical coordinate values. The horizontal coordinate is time t. From this print-out or screen display the tendency for film build-up can be followed. Typically, film thickness increases gradually (arithmetically) to $t_1$ and then accelerates (exponentially) $t_1$ to $t_2$ which calls for a correction by injecting a treating agent to combat the deposited matter. Other analogs of film thickness are possible (vertical axis, FIG. 11) but voltage is by far the easiest to process.

The monitor system described above can be computer controlled. The program to be described below would be typical, first determining the base line intensity of the light beam in air (disc in FIG. 1 position) and also the intensities of the light beam passing through a clean disc at each prospective targeted circle. The beam intensity values for a clean disc are stored as constants.

In the preceding disclosure light intensity is denoted by the symbol i, or i' for ease of discussion and depiction. In the discussion to follow, intensity is given the symbol I along with (defined) subscripts ci and fi, necessitated by the corrections which feature in equation (5). Intensity values can be substituted by voltage (V) emitted by the sensor or detector 22 since I and V are directly proportional to one another.

During initialization at t=0 (time, zero, no monitoring cycle yet commenced) a reading for the intensity (I) of the light beam in air is taken, $I_a(0)$, and stored. Afterwards (t=0) all ten target areas (i in the following equation, Eq. 5) are read for intensity through the clean disc, $I_{ci}$, and stored. Next, at time t, all ten (fouled) target areas ($i_1 \ldots i_{10}$) are successively read, $I_{fi}(t)$, defining a monitoring cycle. Times and date are recorded. The process is repeated for subsequent monitoring cycles at regular intervals set by the software.

The film absorbance for each targeted area is calculated by the computer. Film absorbance, proportioned to film thickness at time t, is given as $A_i(t)$ in the following equation:

$$A_i(t) = \log \frac{I_{ci}I_a(t)}{I_a(0)I_{fi}(t)} \quad \text{(Eq. 5)}$$

where, $I_a(t)$ = measured intensity through air only, at time t. $I_a(O)$ is stored in memory during initialization;

$I_{ci}$ = measured intensity through the clean disc at target area i. These values (e.g., ten); are also stored in memory; and $I_{fi}(t)$ = measured intensity of the fouled disc at target area i at time t.

In other words, consistent with Eq. (4), the absorbance of an area i is log $(I_{ci}/I_{fi})$; but to correct for light intensity drift, dirty optical surfaces, etc., the clean disc intensity, $I_{ci}$, is modified by $I_a(t)/I_a(O)$.

The disc has been referred to as a coupon configuration which is to say it need not be round. Indeed it could be square, but mounted eccentrically. The disc need not be transparent; it can be translucent as long as the quality allows light to be transmitted therethrough. Two homogeneous discs could be used: one entirely hydrophilic and one entirely hydrophobic, in succession, with the cycling timed for long term species (hydrophilic) and short term (hydrophobic).

We claim:

1. Method of monitoring film formers in an opaque fluid comprising:
   (a) immersing in the fluid a segment of a transparent disc having a surface to which the film formers will occlude;
   (b) rotating the disc after a predetermined time of immersion to expose for optical monitoring the previously exposed segment containing the occluded film;
   (c) casting a light beam of known reference intensity on a targeted area of the exposed occluded film, thus presenting a sample for thickness monitoring, and measuring the intensity of the light transmitted through he targeted area and the disc as the sample transmittance intensity; and
   (d) determining the difference between the reference intensity and the sample transmittance intensity as a measure of film thickness.

2. Method according to claim 1 in which the disc has at least two segments presenting surfaces which differ in kind respectively to occlude film formers which differ in kind and subjecting each segment to steps (c) and (d).

3. Method according to claim 2 in which the disc has one segment presenting a surface which is hydrophilic in character and a second segment presenting a surface which is hydrophobic in character.

4. Method according to claim 1 in which the sample transmittance intensity and the reference intensity are converted to voltage analogs V' and V, respectively, and in which the voltage analogs are ratioed, log V/V', as the absorbance of the film equivalent to film thickness.

5. Method according to claim 4 in which log V/V' is plotted as a function of time.

6. Apparatus for determining the tendency for film build-up due to opaque film formers entrained in a body of liquid comprising an eccentrically mounted rotatable transparent disc to be immersed in the body of liquid to occlude a film generated by the film formers, a source of light to be cast on a targeted portion of the occluded film and a detector to detect the intensity of light transmitted through the targeted film and the disc, means to rotate the disc after immersion for a predetermined time to an index position where the targeted area is exposed to the source of light, and means to compare the intensity of light transmitted from the source through the disc when the film is not present to the intensity when the film is present on the disc.

7. Apparatus according to claim 6 in which the disc has both a hydrophilic segment and a hydrophobic segment to be immersed in the body of liquid for a predetermined time period.

* * * * *